(12) United States Patent
Mews et al.

(10) Patent No.: US 8,647,378 B2
(45) Date of Patent: Feb. 11, 2014

(54) MEDICAL IMPLANT, IN PARTICULAR A STENT, FOR IMPLANTATION IN AN ANIMAL BODY AND/OR HUMAN BODY

(75) Inventors: Steffen Mews, Rostock (DE); Frank Bakczewitz, Rostock (DE)

(73) Assignee: Biotronik AG, Buelach (CH)

( * ) Notice: Subject to any disclaimer, the term of this patent is extended or adjusted under 35 U.S.C. 154(b) by 0 days.

(21) Appl. No.: 13/248,731

(22) Filed: Sep. 29, 2011

(65) Prior Publication Data

US 2012/0089217 A1    Apr. 12, 2012

Related U.S. Application Data

(60) Provisional application No. 61/391,085, filed on Oct. 8, 2010.

(51) Int. Cl.
*A61F 2/82* (2013.01)
(52) U.S. Cl.
USPC .......................................... 623/1.15; 623/1.11
(58) Field of Classification Search
None
See application file for complete search history.

(56) References Cited

U.S. PATENT DOCUMENTS

| 5,871,536 | A | * | 2/1999 | Lazarus | 623/1.13 |
| 2003/0040791 | A1 | * | 2/2003 | Oktay | 623/1.17 |
| 2006/0084988 | A1 | * | 4/2006 | Kim | 606/61 |
| 2006/0173527 | A1 | * | 8/2006 | Scherrible | 623/1.15 |

FOREIGN PATENT DOCUMENTS

| DE | 197 28 337 A1 | 7/1999 | |
| EP | 1 557 138 A1 | 7/2005 | |
| WO | 98/53760 A2 | 3/1998 | |
| WO | 2004/045450 A2 | 3/2004 | |
| WO | 2007/131002 A2 | 11/2007 | |
| WO | WO 2010011699 A2 * | 1/2010 | ............... A61F 2/24 |
| WO | 2010/103344 A1 | 9/2010 | |

* cited by examiner

*Primary Examiner* — Thomas J Sweet
*Assistant Examiner* — Rebecca Preston
(74) *Attorney, Agent, or Firm* — Biotech Beach Law Group PC

(57) ABSTRACT

A medical implant (10a, 10b), in particular a stent (12a, 12b), for implantation in an animal body and/or human body (14a, 14b), comprising a base body (16a, 16b) which includes at least two segments (18a, 18a', 18b, 18b'; 20a, 20a', 20b, 20b') having at least two deflection points (24a, 24b; 26a, 26b) that are diametrically opposed in the axial direction (22a, 22b), and at least one adjusting means (28a, 28b; 30a, 30b) that acts on the deflection points (24a, 24b; 26a, 26b) to adjust an extension (32a, 32b) of the base body (16a, 16b) in the circumferential direction (34a, 34b).

15 Claims, 5 Drawing Sheets

MEDICAL IMPLANT, IN PARTICULAR A STENT, FOR IMPLANTATION IN AN ANIMAL BODY AND/OR HUMAN BODY

CROSS REFERENCE TO RELATED APPLICATION

This patent application claims the benefit of U.S. Provisional Patent Application No. 61/391,085, filed on Oct. 8, 2010, which is hereby incorporated by reference in its entirety.

TECHNICAL FIELD

The invention relates to a medical implant, in particular a stent, for implantation in an animal body and/or human body.

BACKGROUND

Implants are used often in medical applications for implantation in an animal body and/or human body permanently or at least for an extended period of time to perform replacement functions. Examples would be e.g. cardiac pacemakers, brain pacemakers for Parkinson's patients, cardiac implants, cochlear implants, retinal implants, dental implants, joint replacement implants, vascular prostheses or stents.

A stent is made known in US 2009/0248136 A1 that comprises serpentine struts, in the case of which the dilation of the stent using a telescoping ratchet mechanism irreversibly changes a length of the respective struts in dilation.

SUMMARY

The object of the invention is to provide an implant that can be dilated exactly and is highly stable.

The invention is directed to a medical implant, in particular a stent, for implantation in an animal body and/or human body, comprising a base body that includes at least two struts having at least two deflection points which are diametrically opposed in the axial direction, and at least one adjusting means, which acts on the deflection points, for adjusting an extension of the base body in the circumferential direction.

It is provided that the adjusting means can be used to shorten an axial distance between the two deflection points. The design according to the invention advantageously makes it possible to provide an implant that can be expanded, using an adjusting means, in a manner that saves costs and installation space, the fully expanded implant having a strong radial force and high stiffness to securely anchor an intended shape of the implant. As a result it is possible to avoid over-dilating an implantation site or a vessel, thereby ensuring safe interaction with tissue. Furthermore, the implantation can be performed in a manner that is safe for the material, thereby ensuring a low failure rate for the implant and, therefore, surgery without complications.

In this context, an "implant" is intended to mean, in particular, a body that functions as a replacement, permanently or at least for a longer period of time, when implanted in an animal body and/or human body. Other possibilities that are feasible in this case are all medical implants that appear suitable to a person skilled in the art, such as cardiac pacemaker, a brain pacemaker, a cardiac implant, a cochlear implant, a retinal implant, a dental implant, a joint replacement implant, or a vascular prosthesis; an embodiment of the medical implant as a stent is particularly advantageous. By designing the implant as a stent, or given that the base body includes a stent, a structure can be provided that is easily implanted.

Furthermore, a "base body" in this context is intended to mean, in particular, a structure such as a wire mesh that substantially imparts a shape and/or form to the implant or, in particular, imparts a shape to the stent, or forms the stent itself. In addition, the base body is preferably composed of a metallic material and/or a combination of a plurality of metallic materials, such as iron, magnesium, nickel, tungsten, titanium, zirconium, niobium, tantalum, zinc, silicon, lithium, sodium, potassium, manganese, and/or any other material that appears reasonable to a person skilled in the art. Another possibility would be a zinc-calcium alloy and/or a material having a memory effect, such as a copper-zinc-aluminum alloy and/or a nickel-titanium alloy, preferably Nitinol. As an alternative, it can be advantageous for the base body to include, at the least, cobalt and/or chromium, preferably in the form of stainless steel and/or a Cr—Ni—Fe steel—preferably the alloy 316L in this case—or a Co—Cr alloy. Using this embodiment, an implant can be provided that has good dilatability and advantageous flexibility combined with high stability. Basically, it would also be feasible, however, for the base body of the implant to be composed at least partially of plastic, a ceramic, and/or a biodegradable material.

Furthermore, a "segment" refers, in particular, to a structure of the base body that extends in the circumferential direction of the implant and/or has a serpentine or wavy shape and/or is formed by a stent strut. In this context, a "deflection point" refers, in particular, to a point on the segment at which the direction of the segment changes. Advantageously, the deflection point is a minimum or a maximum in the extension of the segment in the axial direction of the implant. In this case, maxima that are situated at the same level in the circumferential direction or belong to segments that are diametrically opposed in the axial direction and are adjacent to each other in the axial direction can both be maxima or is minima, or a maximum and a minimum. Preferably, however, a minimum is opposite a maximum and, particularly preferably, the minima of a first segment are connected, preferably bonded, to the maxima of a second segment, thereby forming a contact point. The base body is therefore composed of cells. These cells can have any shape that appears suitable to a person skilled in the art, such as round, oval, rectangular, and/or diamond-shaped. This shape is designed to be foldable in particular. Particularly preferably, the cells are substantially diamond-shaped. In this context, the expression "substantially diamond-shaped" is intended to mean, in particular, that shapes that are similar to a diamond or a rhombus, such as a diamond-like shape having rounded corners and/or concave and/or convex sides, can also be referred to as "diamond-shaped". When the implant is in the folded-together state, the minima and maxima preferably each form an acute angle.

In this context, an "adjusting means" is intended to mean, in particular, a means for adjusting the at least one parameter, such as a contour, an extension, a length, and/or a diameter of the implant. In particular, the adjusting means adjusts at least one extension of the base body in the circumferential direction and, therefore, a cross section of a surface perpendicular to the axial direction of the base body, and an axial length of the base body. In this context, the expression "which acts on the deflection points" is intended to mean, in particular, that forces, in particular adjusting forces of adjusting means, are transferred via the segments in particular to the deflection points, and/or that the adjusting means have direct contact to the deflection points, in particular via the segments. In this case, the adjusting means are not, in particular, an expansion means in the form of a balloon catheter and/or a property of self-expansion of an implant, in particular using a memory-effect material. The axial length of the base body can also be shortened, according to the invention, by shortening the axial distance between the deflection points using the deflection means. This can be achieved using a particularly simple design e.g. by using the diamond-shaped cells.

It is furthermore provided that the adjusting means are a second expansion means, and first to expansion means are provided that can be used separately from the second expansion means. In this context, an expansion means refers, in particular, to a means that expands the implant or the base body i.e. enlarges the cross section of the surface perpendicular to the axial direction of the base body. Furthermore, a "first expansion means" refers, in particular, to a balloon catheter and/or a property of self-expansion of the implant, in particular using a memory-effect material and/or any other means that appears suitable to a person skilled in the art. In this case, "can be used" means, in particular, can be operated, designed, and/or implemented, and the expression "can be used separately" means, in this context in particular, that the two expansion means are composed of different components and/or are operated using different expansion mechanisms and/or that the expansion mechanism of the second expansion means is independent of the expansion of the base body carried out using the first expansion means. Furthermore, "provided" is intended to mean specially equipped, designed, embodied, and/or prepared. Using the two expansion means, different expansion mechanisms can be advantageously used, thereby resulting in an implant that is particularly versatile.

Advantageously, the second expansion means are designed to be expanded after the first expansion means. The expression "after" is intended to mean subsequently, in particular. The delay advantageously provides the time required to fine-tune and secure the positioning achieved after the initial expansion. The adjusting means and/or the second expansion means are therefore used to fix an expanded shape and/or intended shape of the base body in position.

The expansion of a balloon-expandable stent is generally followed by a recoil or an elastic retraction of the stent, the compensation of which can result in an overdilation of the implant site. According to a further embodiment of the invention the adjusting means therefore has a rigid length, thereby preventing recoil when the first expansion means is expanded. In this context, a "rigid length" refers, in particular, to an unchangeable and/or fixed length, in particular in the axial direction of the adjusting means, and "preventing" means reducing and/or advantageously avoiding. Preventing recoil can ensure that the interaction with the implant site is gentle while also reducing material load, thereby increasing the reliability of the implant. Furthermore, a position of the implant can be adapted exactly to a dimension of the implant site, thereby resulting in a secure, exact seat.

It is furthermore advantageous for the adjusting means to extend in the axial direction along an axial length of the base body. The adjusting means preferably extend along the entire axial length of the base body. By way of this embodiment, a mode of operation of the adjusting means can be combined with the implant in an overall simple design.

It is furthermore provided that the implant include at least one passage which is disposed on at least one deflection point and is provided for the adjusting means. In this context, a "passage" is intended to mean, in particular, a recess having a smooth inner wall, through which the adjusting means extends. To this end, two deflection points, as the maximum and the minimum, that are connected to each other preferably include passages that are aligned in a flush manner. Basically, a plurality of such passages which are extended through can be provided along the axial length of the adjusting means. The passage makes it possible to integrate the adjusting means into the base body using a simple design and without interference.

In addition, it is advantageous to provide recesses in the axially outward segments of the base body, the recesses facing each other and being designed e.g. as blind holes for receiving axial ends of the adjusting means, thereby preventing the adjusting means from extending beyond the axial length of the implant or the base body and minimizing irritation of surrounding tissue.

Furthermore, it can be advantageous for the implant to include at least two adjusting means which are distributed in the circumferential direction around a circumference of the base body, thereby ensuring that the base body can be advantageously shortened in the axial direction homogeneously around the circumference of the implant, thereby preventing the implant from becoming tilted, disadvantageously, at the implant site. Furthermore, it is advantageous for the adjusting means to be distributed symmetrically around the circumference and, expediently, to extend parallel to each other, thereby ensuring that the movement imparted by the adjusting means is uniform. Basically, a number of adjusting means can be increased until each contact point between a maximum and a minimum includes a recess and/or a pair of passages, thereby ensuring that adjustment is implemented in a particularly uniform manner.

A simple and uncomplicated functionality and/or a simple operation of the adjusting means can be advantageously achieved when the adjusting means includes at least one actuator starting point for an actuator. In this context, an "actuator starting point" refers, in particular, to a shaping, such as a projection, a bolt, a hexagon bolt, a slot, a cross recession, and/or another shaping that appears reasonable to a person skilled in the art, into and/or onto which an actuator, such as a drill, a wrench, a ratchet wrench, a crank, and/or another type of actuator that appears reasonable to a person skilled in the art can be applied to operate the adjusting means. Advantageously, the actuator starting point is provided for an externally operated actuator i.e. the actuator preferably can be operated from outside the body, thereby ensuring that the adjusting means are particularly simple to operate. The actuator starting point is disposed on an axially outwardly facing end of the adjusting means. The recess in the axially outer segment which is disposed on an end of the base body facing away from an implantation direction is a continuous recess and is extended through by the end of the adjusting means having the actuator starting point in a manner such that the adjusting means terminates flush with the axial end of the base body or a recess in the axial outer surface of the first segment.

It is also provided that the adjusting means include at least two components which can be screwed together. These components preferably have complementary threads and are secured in the axially outer segments of the base body. Advantageously, a first component has an internal thread and/or is designed as a cylinder which can be fastened or screwed into the recess located in the outer segment disposed on an end of the base body that points in the implantation direction. A second component, which is preferably designed as a rod that extends through the recess(es), is secured in the recess located in the axially outer segment in the end of the base body that faces away from the implantation direction. The second component is secured in a manner that allows it to rotate. Furthermore, the second component includes an external thread on an end that is diametrically opposed to the end having the actuator starting point. When the adjusting means are adjusted, the two components are screwed into each other in a manner such that their total combined length and the length of the stent cells are shortened. The embodiment according to the invention enables the adjusting means to be realized using a simple structure and a reliable design.

Basically, it would also be possible for the component having the internal thread to be an internal thread itself that is formed in the recess located in the axially outer segment in the end of the base body that faces the implantation direction. In this case, the recess is designed as a blind hole in order to limit the screw-in depth. In principle, it would also be feasible to include internal threads in the passage(s) and the recess in the axially outer segment disposed on the end of the base body facing away from the implantation direction, and to screw a threaded rod into it, to shorten the axial distance. However, to protect the region surrounding the implant, a means would have to be provided for covering the overhang of the threaded rod beyond the recess.

According to a preferred development, at least one of the components includes at least one unthreaded section for centering the components which can be screwed together, when expansion is carried out using the first expansion means. Expediently, the unthreaded section is located on the first component, and is designed as a smooth cylindrical sleeve. Advantageously, the second component engages via its end having the external thread in the unthreaded section in the unexpanded state of the implant. As a result, the two components can glide over each other in a captive manner during the first expansion e.g. using a balloon catheter, thereby ensuring that the positions of the two components required for the screwing-in can be adjusted using a reliable process.

According to a further embodiment of the invention, the adjusting means have a diameter of at least 200 μm, preferably at least 400 μm, and particularly advantageously at least 500 μm. The adjusting means are advantageously adapted to the dimensions of the implant with e.g. stent struts having a wall thickness of approximately 600 μm, and a stable structure can be provided.

It is furthermore provided that the adjusting means include a first component and at least one second component, the components being designed as twistable wires, thereby resulting in low-cost, low-weight, and non-complex adjusting means.

It is also provided that the base body include a stabilizing body for a bone, in particular a vertebral body. The implant is preferably designed as a vertebral body stent. By way of this embodiment according to the invention, an easy-to-use, reliable implant can be realized for use in applications that require implants that are particularly robust and dimensionally stable.

DESCRIPTION OF THE DRAWINGS

The invention is explained in the following in greater detail with reference to embodiments that are depicted in drawings. They show.

DETAILED DESCRIPTION

Figure 1:
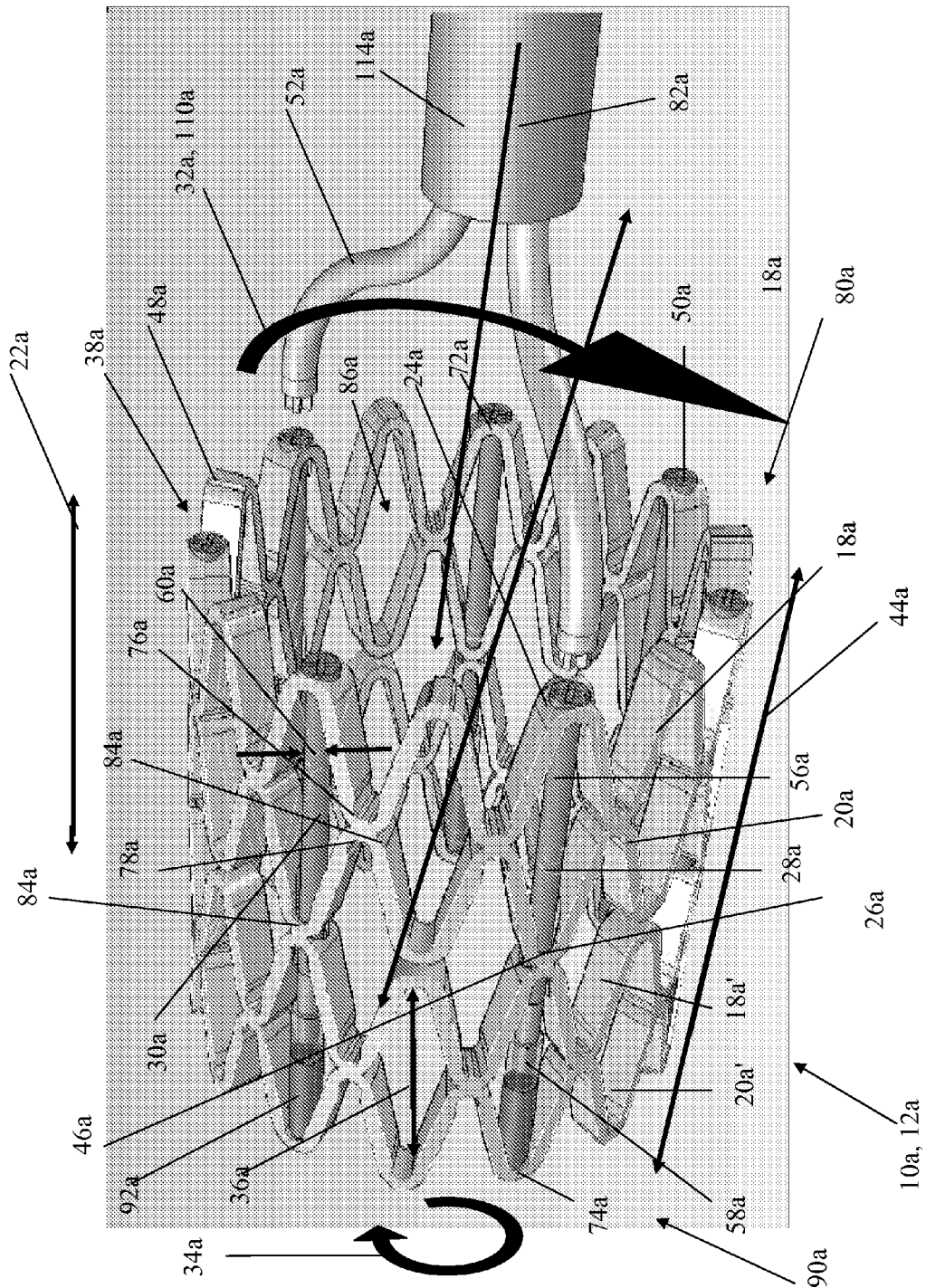
FIG. 1 an implant according to the invention, in a perspective view, with an actuator device, FIG. 2 a detailed view of the implant depicted in FIG. 1, before it is expanded using the adjusting means, FIG. 3 a detailed view of the implant depicted in FIG. 1, after it is expanded using the adjusting means.

Elements that are functionally identical or similar-acting are labeled using the same reference numerals in the figures. The figures are schematic depictions of the invention. They do not depict specific parameters of the invention. Furthermore, the figures merely show typical embodiments of the invention and should not limit the invention to the embodiments shown.

Regarding elements in a figure that are not described further, reference is made to the respective description of the elements in preceding figures to avoid unnecessary repetition.

FIG. 1 shows, in a perspective view, a medical valve implant 10a designed as a stent 12a for implantation in an animal body and/or human body 14a (see FIG. 4), having a base body 16a which comprises stent 12a and contains, as the material, a medical stainless steel and/or a chromium-cobalt alloy. Base body 16a includes, as the base body structure, a wire mesh that is formed by serpentine segments 18a, 18a', 20a, 20a' or stent struts 70a in a manner known to a person skilled in the art. Segments 18a, 18a', 20a, 20a' extend in a circumferential direction 34a around a circumference 48a of base body 16a and are disposed one after the other in an axial direction 22a. Each segment 18a, 18a', 20a, 20a' has minima 72a and maxima 74a that are situated in alternation around circumference 48a, each forming a deflection point 24a, 26a, 76a, 78a. In each case, maxima 74a of segment 18a, which forms a first segment and is disposed on an end 80a of base body 16a that faces away from an implantation direction 82a, and minima 72a of segment 20a, which forms a second segment, are diametrically opposed in axial direction 22a, and therefore deflection points 24a are likewise diametrically opposed. Minima 72a of first segment 18a and maxima 74a of second segment 20a adjoin each other in axial direction 22a, forming a contact point 84a in each case, at which segments 18a, 20a are bonded. Similar contact points 84a are also formed between minima 72a of second segment 20a and maxima 74a of a third segment 18a'. In principle, this structure can continue in axial direction 22a to any extent, although only four segments 18a, 18a', 20a, 20a' are shown here.

Due to this design, the wire mesh and/or base body 16a includes a plurality of cells 86a which are substantially diamond-shaped and are disposed next to each other in circumferential direction 34a and one behind the other in axial direction 22a. When implant 10a is in the folded state, minima 72a and maxima 74a and, therefore, deflection points 24a, 26a form acute angles 88a of the diamonds. This design enables implant 10a to be folded and, when expanded, cells 86a expand in circumferential direction 34a, while their extension in axial direction 22a shortens.

In addition, base body 16a comprises a plurality of adjusting means 28a, 30a that act on deflection points 24a, 26a to adjust an extension 32a of base body 16a in circumferential direction 34a. Adjusting means 28a, 30a are distributed in circumferential direction 34a around circumference 48a of base body 16a, or seven adjusting means 28a, 30a, in this case, are distributed evenly around circumference 48a, each separated by approximately 50°, and are situated parallel to each other. Furthermore, adjusting means 28a, 30a extend in axial direction 22a along an axial length 44a of base body 16a and have the same length in axial direction 22a as base body 16a from a maximum 74a of first segment 18a and a minimum 72a of fourth segment 20a' which is disposed on an end 90a of base body 16a that faces implantation direction 82a. Furthermore, adjusting means 28a, 30a have a diameter 60a of 500 μm, which is of the same magnitude as the wall thickness of stent struts 70a, which is approximately 600 μm.

Figure 2:
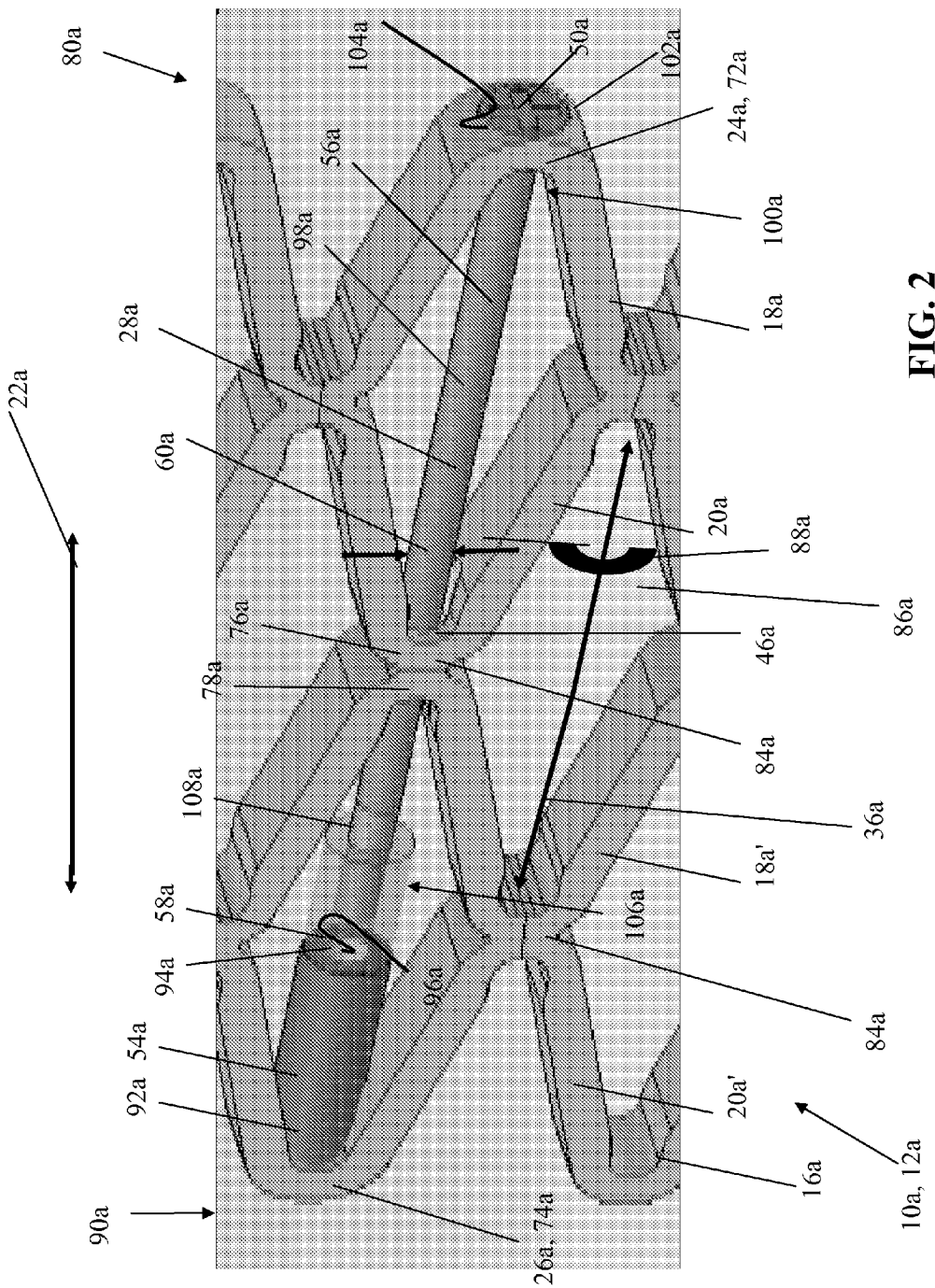

Moreover, base body 16a of implant 10a includes passages 46a that are disposed in deflection points 24a, 26a and are provided for adjusting means 28a, 30a (see also FIG. 2).

Passages 46a are formed in contact points 84a between minima 72a of second segment 20a and maxima 74a of third segment 18a' as aligned recesses having smooth inner surfaces. Adjusting means 28a, 30a include components 54a; 56a, which can be screwed together, first component 54a being formed by a cylinder 92a which has an internal thread 96a in a blind hole 94a. Cylinder 92a is disposed at deflection point 26a i.e. on a side of minimum 72a of fourth segment 20a' facing away from implantation direction 82a, and is fastened in a not-shown recess in minima 72a e.g. using a bolt which is not shown. In addition, an unthreaded section 58a is integrally formed or designed on first component 54a, in the form of a smooth cylindrical sleeve section for centering components 54a, 56a, which can be screwed together, when expansion is carried out using a first expansion means 38a.

Second component 56a is designed as a rod 98a that extends through recess 46a and is secured via an end section 100a in a recess 102a that extends through deflections 24a and/or maxima 74a of segment 18a. End section 100a is flush with base body 16a and/or an axial outer surface 104a of segment 18a. Furthermore, second component 56a includes, on an end 106 that is diametrically opposed to end section 100a, an external thread 108a that corresponds with internal thread 96a of first component 54a. An actuator starting point 50a for an actuator 52a or an externally operated actuator 52a which is designed as a crank 110a is integrally formed on end section 100a of rod 98a or adjusting means 28a, 30a, actuator starting point 50a being designed as a cross recession and facing away from implantation direction 82a.

Figure 4:
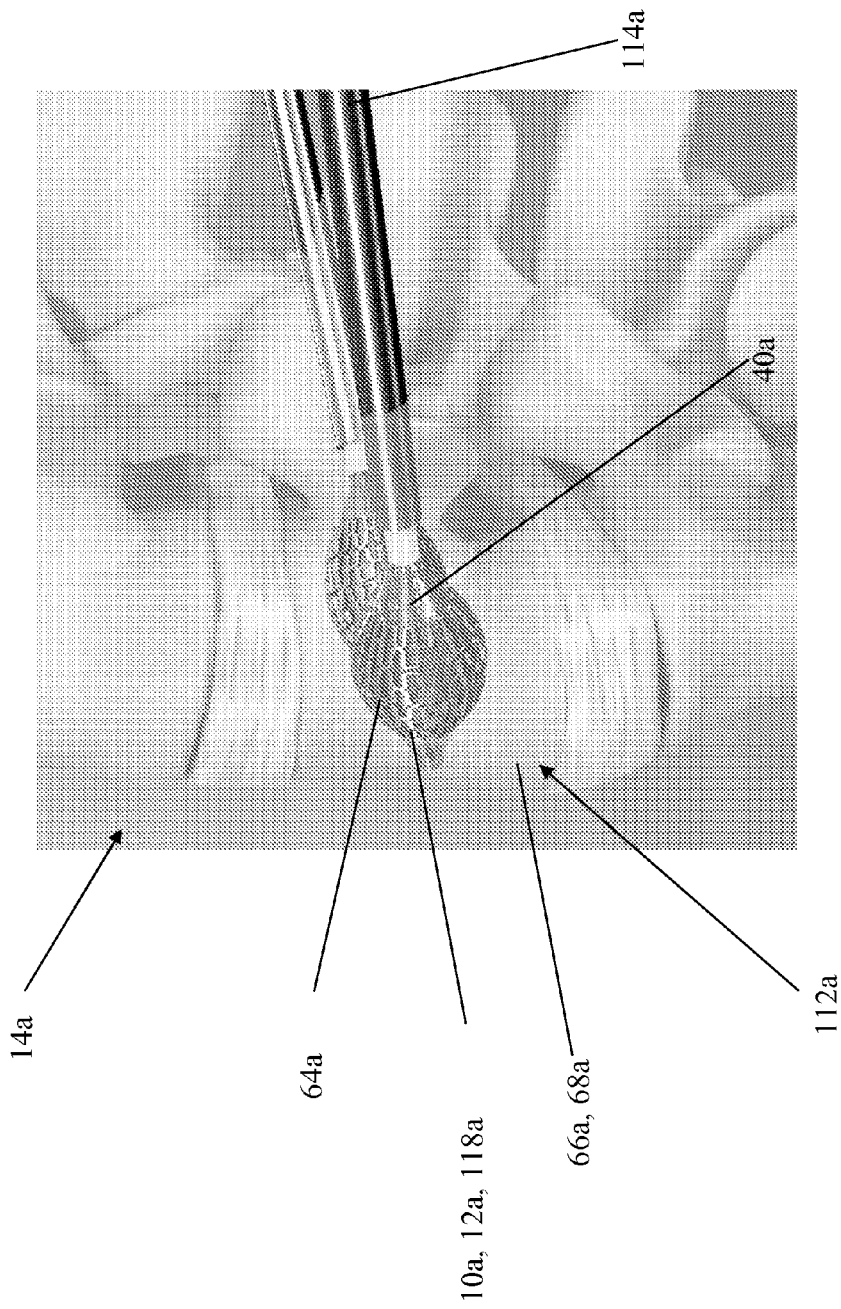
FIG. 4 shows a schematic depiction of the implant at an implantation site.

Adjusting means 28a, 30a are a second expansion means 38a which can be used to position implant 10a once it has been initially positioned at an implantation site 112a (see FIG. 4). The predilation or pre-positioning is performed using a first expansion means 40a which is designed as a not-shown balloon catheter and can be used separately from second expansion means 38a. Adjusting means 28a, 30a and/or second expansion means 38a are therefore designed to be expanded after first expansion means 40a.

FIG. 2 shows a section of implant 10a having an adjusting means 28a in the state after expansion was performed using first expansion means 40a. End 106a having external thread 108a of second component 56a is situated and centered in unthreaded section 58a of first component 54a. This took place when dilation was performed using first expansion means 40a since sections 58a, 108a can glide relative to each other and can be slid into each other.

Now, as indicated in FIG. 1, if actuator point 50a is actuated using actuator 52a or crank 100a having two arms, actuator point 50a having been guided toward stent 12a using an implantation device 114a designed as a cannula, external thread 108a rotates in internal thread 96a of blind hole 94a of first component 52a. This is carried out for each adjusting means 28a, 30a or for each pair of adjusting means 28a, 30. The screwing process is performed until stent 12a has reached its desired position or until end 106a of rod 98a impacts blind hole 94a. Once this occurs, crank 110a is withdrawn through the channel.

Figure 3:
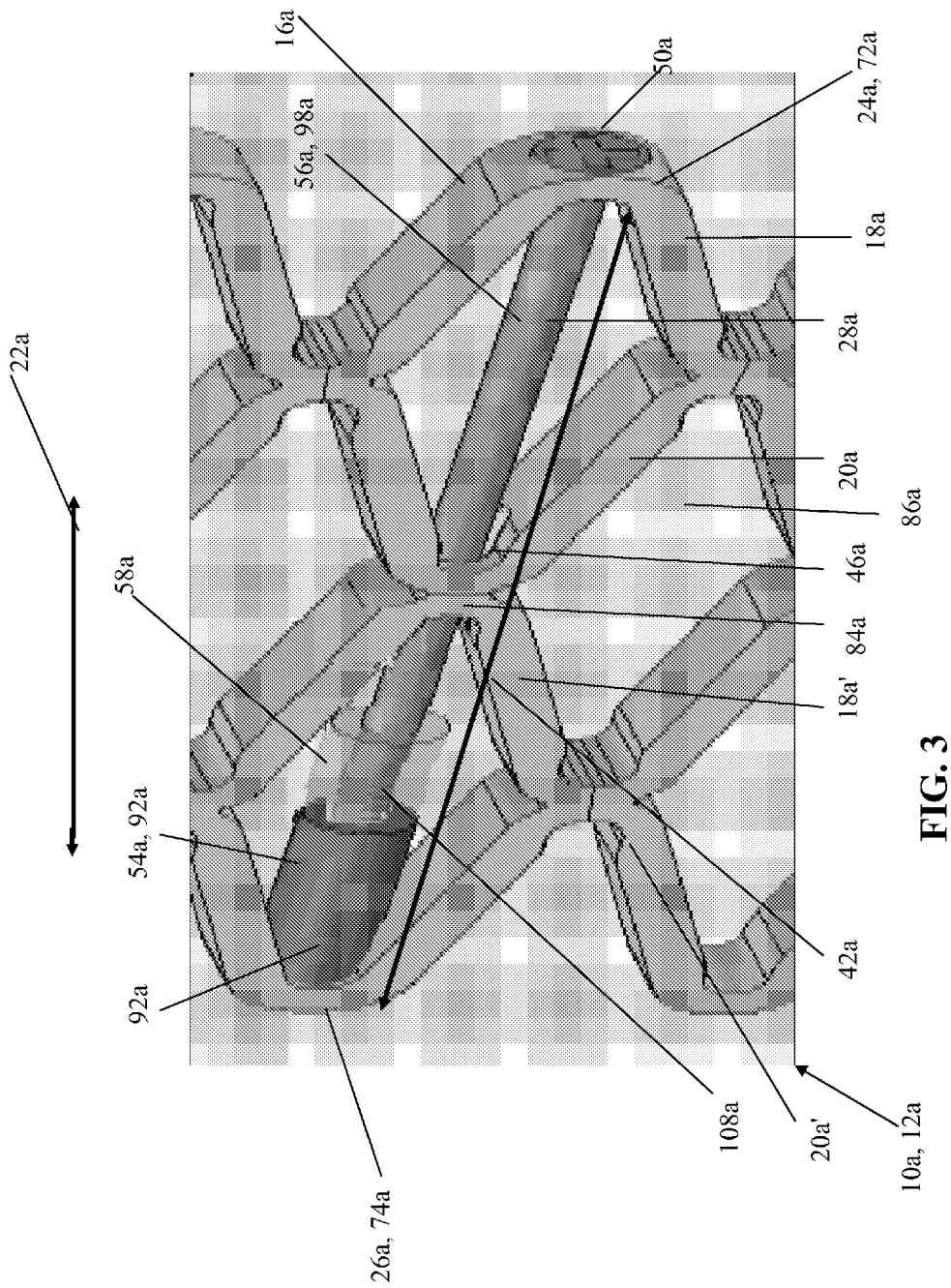

FIG. 3 shows the same section of implant 10a as in FIG. 2 after expansion has been performed using second expansion means 38a. When components 54a, 56a are screwed together using adjusting means 28a, 30a, a common length of components 54a, 56a decreases, thereby shortening an axial distance 36a between the two deflection points 24a, 26a. As a result, cells 86a through which adjusting means 28a, 30a extend are forced to open in circumferential direction 34a. Adjacent cells 86a that do not have adjusting means are also influenced by this, and their diamond shape likewise changes. As a result, a stent shape similar to a cuboid, for instance, can also be provoked (although this is not depicted.)

Furthermore, due to securely screwed-in component 54a, 56a, adjusting means 28a, 30a have a rigid length 42a for securing stent 12a in its end position, thereby preventing recoil from occurring—or at least ensuring that it does not come into play—when first expansion means 40a are expanded, since the final position of stent 12a can be adjusted without recoil using adjusting means 28a, 30a. Adjusting means 28a, 30a therefore make it possible to expand a cross section 116a of a surface of base body 16a that is situated perpendicularly to axial direction 22a of base body 16a, and to therefore adapt the stent shape to particular circumstances or a dimension of implantation site 112a without unnecessarily stressing implantation site 112a with a recoil.

Stent 12a is designed as a vertebral body stent 118a and is implanted in a collapsed vertebral body 68a. FIG. 4 shows a schematic depiction of implantation site 112a, including implanted implant 10a and implantation device 114a. Once stent 12a has been secured in the desired position, it is cemented and can thereby stabilize defective vertebral body 68a, and base body 16a therefore includes a stabilizing body 64a for a bone 66a or vertebral body 68a. It would be advantageous, for example, for stent 12a to assume a cuboid shape in order to increase the stability of stent 12a.

Figure 5:
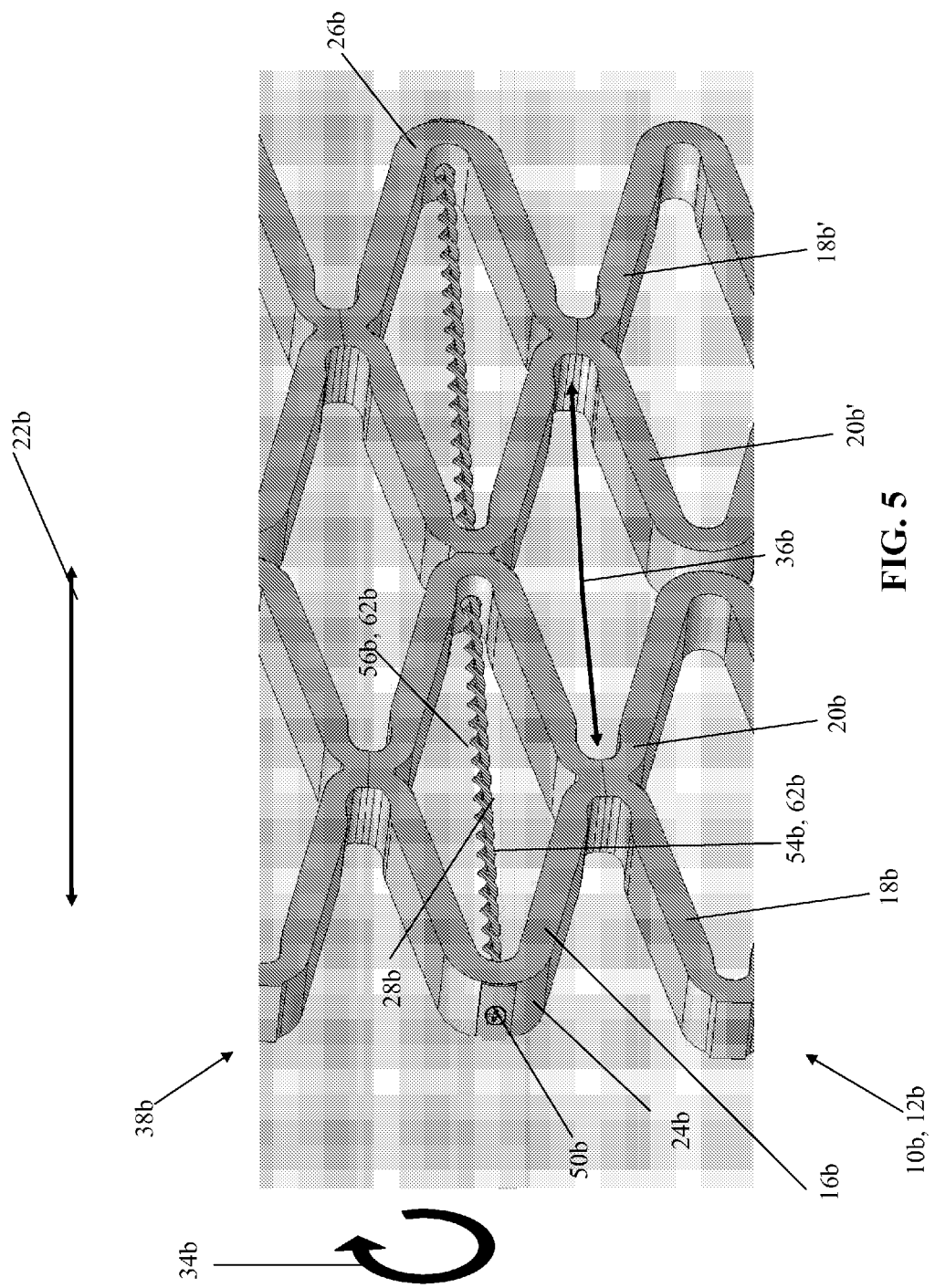
FIG. 5 shows a detailed view of an alternative embodiment of the implant.

An alternative embodiment of medical implant 10a is depicted in FIG. 5. Components, features, and functions that are essentially the same are labeled with the same reference numerals. To distinguish the embodiments from one another, the reference numerals of the embodiments are appended with the letters a and b. The description that follows is limited mainly to the differences from the embodiment presented in FIGS. 1 through 4, and reference is made to the description of the embodiment shown in FIGS. 1 through 6 with regard for the components, features, and functions that remain the same.

FIG. 5 shows a section of an alternative medical implant 10b in the form of a stent 12b or a vertebral body stent 118a having a base body 16b with segments 18b, 20b which have deflection points 24b, 26b that are diametrically opposed in axial direction 22a, and adjusting means 28b that extend through a passage 46b and act on deflection points 24b, 26b. Adjusting means 28b and/or a second adjusting means 30b, which are not depicted here, are designed as second expansion means 38a and include a first component 54b and a second component 56b, wherein components 54b, 56b are designed as twistable wires 62b. Twisting wires 62b using a not-shown actuator at an actuator starting point 50b shortens an axial distance 36b between deflection points 24b, 26b. As a result, a diamond structure of a cell 86b of base body 16b changes, thereby enabling an extension 32b of base body 16b to be adjusted and/or enlarged in circumferential direction 34b.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE CHARACTERS

10 Implant
12 Stent
14 Body
16 Base body
18 Segment
20 Segment
22 Direction
24 Deflection point
26 Deflection point
28 Adjusting means
30 Adjusting means
32 Extension
34 Circumferential direction
36 Distance
38 Expansion means
40 Expansion means
42 Length
44 Length
46 Passage
48 Circumference
50 Actuator starting point
52 Actuator
54 Component
56 Component
58 Section
60 Diameter
62 Wire
64 Stabilizing body
66 Bone
68 Vertebral body
70 Stent strut
72 Maxima
74 Minima
76 Deflection point
78 Deflection point
80 End
82 Implantation direction
84 Contact point
86 Cell
88 Angle
90 End
92 Cylinder
94 Blind hole
96 Internal thread
98 Rod
100 End section
102 Recess
104 Outer surface
106 End
108 External thread
110 Crank
112 Implantation site
114 Implantation direction
116 Cross section
118 Vertebral body stent

What is claimed is:

1. A medical implant for implantation in an animal body and/or human body, comprising:
a base body which includes at least four segments disposed one after another in an axial direction, each segment having a deflection point, wherein the deflection point of each of two of the at least four segments are diametrically opposed in the axial direction and another two of the at least four segments are bonded together at a contact point, wherein the contact point comprises a passage,
a first adjusting mechanism that passes through the passage and acts on the deflection point of each of the two segments that are diametrically opposed to adjust an extension of the base body in a circumferential direction, characterized in that an axial distance between the deflection point of each of the two segments that are diametrically opposed can be shortened using the first adjusting mechanism; and
at least a second adjusting mechanism, wherein the first and second adjusting mechanisms are distributed in the circumferential direction around a circumference of the base body.

2. The medical implant according to claim 1, characterized in that the first and second adjusting mechanisms extend in the axial direction along an axial length of the base body.

3. The medical implant according to claim 1, characterized in that the first and second adjusting mechanisms have at least one actuator starting point for an actuator, preferably an actuator starting point for an externally operated actuator.

4. The medical implant according to claim 1, characterized in that the first and second adjusting mechanisms comprise at least two components which can be screwed together.

5. The medical implant according to claim 4, characterized in that at least one of the components includes at least one unthreaded section for centering the components, which can be screwed together, when expansion is carried out using a first expansion means.

6. The medical implant according to claim 1, characterized in that the first and second adjusting mechanisms have a diameter of at least 500 μm.

7. The medical implant according to claim 1, characterized in that the base body includes a stabilizing body for a bone, in particular a vertebral body.

8. A balloon catheter in combination with a stent, for implantation in an animal body and/or human body, the stent comprising:
a base body which includes at least four segments disposed one after another in an axial direction, each segment having a deflection point, wherein the deflection point of each of two of the at least four segments are diametrically opposed in the axial direction and another two of the at least four segments are bonded together at a contact point, wherein the contact point comprises a passage, and
an adjusting mechanism that passes through the passage and acts on the deflection point of each of the two segments that are diametrically opposed to adjust an extension of the base body in a circumferential direction, characterized in that an axial distance between the deflection point of each of the two segments that are diametrically opposed can be shortened using the adjusting mechanism.

9. The balloon catheter with medical implant according to claim 8, characterized in that the adjusting mechanism adjusts the extension of the base body after expansion of the balloon catheter.

10. The balloon catheter with medical implant according to claim 8, characterized in that the adjusting mechanism has a rigid length, thereby preventing recoil from occurring when the balloon catheter is expanded.

11. The balloon catheter with medical implant according to claim 8, characterized in that the adjusting mechanism extends in the axial direction along an axial length of the base body.

12. The balloon catheter with medical implant according to claim 8, characterized in that the adjusting mechanism has at least one actuator starting point for an actuator, preferably an actuator starting point for an externally operated actuator.

13. The balloon catheter with medical implant according to claim 8, characterized in that the adjusting mechanism comprises at least two components which can be screwed together.

14. The balloon catheter with medical implant according to claim 13, characterized in that at least one of the components includes at least one unthreaded section for centering the components, which can be screwed together, when expansion is carried out using a first expansion means.

15. The balloon catheter with medical implant according to claim 8, characterized in that the adjusting mechanism has a diameter of at least 500 μm.

* * * * *